United States Patent [19]

Inaba et al.

[11] 4,099,002
[45] Jul. 4, 1978

[54] QUINAZOLINONE DERIVATIVES AND A PROCESS FOR PRODUCTION THEREOF

[75] Inventors: Shigeho Inaba, Takarazuka; Michihiro Yamamoto, Toyonaka; Kikuo Ishizumi, Ikeda; Kazuo Mori, Kobe; Masao Koshiba, Takarazuka; Hisao Yamamoto, Nishinomiya, all of Japan

[73] Assignee: Sumitomo Chemical Company, Limited, Osaka, Japan

[21] Appl. No.: 495,829

[22] Filed: Aug. 8, 1974

Related U.S. Application Data

[63] Continuation of Ser. No. 207,537, Dec. 13, 1971, abandoned.

[30] Foreign Application Priority Data

Dec. 23, 1970 [JP] Japan ............................ 45-118332
Jan. 19, 1971 [JP] Japan ............................ 46-1477
May 21, 1971 [JP] Japan ............................ 46-34897

[51] Int. Cl.$^2$ .......................................... C07C 295/00
[52] U.S. Cl. .................................. 544/119; 544/116; 544/284; 544/286; 424/251
[58] Field of Search ................. 260/251 QB, 247.2; 544/119

[56] References Cited

U.S. PATENT DOCUMENTS 3,819,627  1/1974  Ott ........................... 260/251 QB

OTHER PUBLICATIONS

Degering; Ed. F., Organic Nitrogen Compounds, University Lithoprinters, 1950, p. 203.
Schwoegler; Ed. J., JACS, 61, pp. 3499–3500, 1939.

Primary Examiner—Paul J. Killos
Attorney, Agent, or Firm—Stevens, Davis, Miller & Mosher

[57] ABSTRACT 3,4-Dihydro-2(1H)-quinazolinone derivatives of the formula,

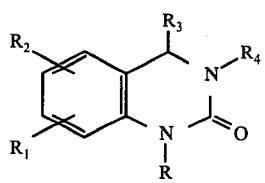

wherein $R_1$ and $R_2$ signify individually a hydrogen atom, a lower alkyl group, a lower alkoxy group, a nitro group, a trifluoromethyl group, a lower alkylthio group, a lower alkylsulfonyl group or a halogen atom; $R_3$ signifies a phenyl group, a halophenyl group, a lower alkylphenyl group, a lower alkoxyphenyl group, a trifluoromethylphenyl group, a lower cycloalkyl group, a lower cycloalkenyl group, a pyridyl group, a pyrrolyl group, a furyl group, a thienyl group or a naphthyl group; $R_4$ signifies a lower alkyl group, a lower alkenyl group, an aralkyl group, a lower cycloalkylalkyl group, a lower cycloalkyl group, a lower alkoxyalkyl group, a lower alkylthioalkyl group, a lower hydroxyalkyl group, a lower alkanoyloxyalkyl group, a phenyl group, a halophenyl group, a trifluoromethylphenyl group, a lower alkylphenyl group a lower alkoxyphenyl group, a pyridyl group or a group of the formula

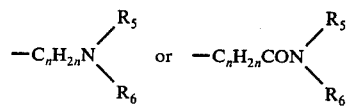

wherein $n$ signifies an integer of 1 to 4; and $R_5$ and $R_6$ signify individually a lower alkyl group, provided that they may form together with the adjacent nitorgen atom an optionally substituted 5- or 6-membered heterocyclic ring, which may further contain a hetero atom); and R signifies a hydrogen atom, a lower alkyl group, a lower alkenyl group, a lower alkoxyalkyl group, a lower alkylthioalkyl group, an aralkyl group, a lower cycloalkylalkyl group, a lower trihalomethylalkyl group or a group of the formula

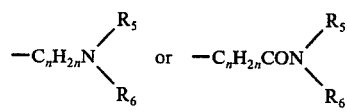

(wherein $n$, $R_5$ and $R_6$ signify the same as defined above), which have excellent pharmacological properties such as central nervous system depressant, anti-inflammatory, analgesic and anti-microbial activities, can be produced by reducing a compound of the formula,

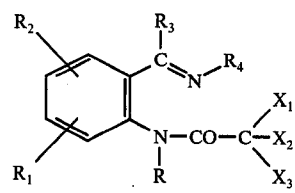

wherein R, $R_1$, $R_2$, $R_3$ and $R_4$ have the same meanings as defined above; and $X_1$, $X_2$ and $X_3$ signify individually a halogen atom, or by the substitution reaction of the ring nitrogen atom of a 1 or 3-unsubstituted 3,4-dihydro-2(1H)-quinazolinone derivative.

11 Claims, No Drawings

QUINAZOLINONE DERIVATIVES AND A PROCESS FOR PRODUCTION THEREOF

This is a continuation of application Ser. No. 207,537 filed Dec. 13, 1971 now abandoned.

This invention relates to a novel process for producing quinazolinone derivatives and to novel quinazolinone derivatives.

More particularly, the invention pertains to a process for preparing 3,4-dihydro-2(1H)-quinazolinone derivatives represented by the formula,

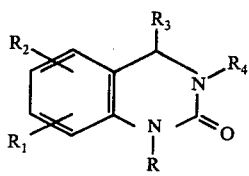

wherein $R_1$ and $R_2$ signify individually a hydrogen atom, a lower alkyl group, a lower alkoxy group, a nitro group, a trifluoromethyl group, a lower alkylthio group, a lower alkylsulfonyl group or a halogen atom; $R_3$ signifies a phenyl group, a halophenyl group, a lower alkylphenyl group, a lower alkoxyphenyl group, a trifluoromethylphenyl group, a lower cycloalkyl group, a lower cycloalkenyl group, a pyridyl group, a pyrrolyl group, a thienyl group, a furyl group or a naphthyl group; $R_4$ signifies a lower alkyl group, a lower alkenyl roup, an aralkyl group, a lower cycloalkyl group, a lower cycloalkylalkyl group, a lower alkoxyalkyl group, a lower hydroxyalkyl group, a lower alkylthioalkyl group, a lower alkanoyloxyalkyl group, a phenyl group, a halophenyl group, a lower alkylphenyl group, a lower alkoxyphenyl group, a trifluoromethylphenyl group, a pyridyl group, or a group of the formula

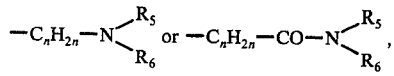

wherein $n$ represents an integer of 1 to 4; $R_5$ and $R_6$ each represents a lower alkyl group, and they may form together with the adjacent nitrogen atom an optionally substituted five or six-membered heterocyclic ring, which may further contain a hetero atom; and R signifies a hydrogen atom, a lower alkyl group, a lower alkenyl group, a lower cycloalkylalkyl, a lower alkoxyalkyl group, a lower alkylthioalkyl group, an aralkyl group, a lower trihalomethylalkyl group, or a group of the formula

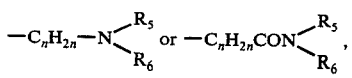

wherein $n$, $R_5$ and $R_6$ signify the same as defined above; and pharmaceutical use of the same.

In the compounds represented by the formula (I), the term "alkyl" means both straight and branched chain aliphatic hydrocarbon radicals, and the lower alkyl group includes, for example, methyl, ethyl, n-propyl, isopropyl, n-butyl, isobutyl and tert-butyl groups; the lower alkoxy group includes, for example, methoxy, ethoxy, n-propoxy, isopropoxy, n-butoxy and tert-butoxy groups; the lower alkylthio group includes, for example, methylthio, ethylthio and isopropylthio groups; the term halogen comprehends all halogens (e.g. fluorine, chlorine, bromine and iodine); the lower cycloalkyl group includes, for example, cyclopropyl, cyclobutyl, cyclopentyl and cyclohexyl groups; the lower cycloalkenyl group includes, for example, cyclopentenyl and cyclohexenyl groups; the lower alkenyl group includes, for example, allyl, methallyl, 2-butenyl, 3-butenyl and 3,3-dimethylallyl groups; the aralkyl group includes, for example, benzyl, phenethyl, chlorobenzyl, fluorobenzyl, methylbenzyl and methoxybenzyl groups; the lower hydroxyalkyl group includes, for example, 2-hydroxyethyl, 3-hydroxypropyl, 2-hydroxypropyl, 2,3-dihydroxypropyl, 1-hydroxymethylethyl and 1-hydroxymethylpropyl groups; the lower alkanoyloxy group includes, for example, acetoxy and propionyloxy groups; and the trihalomethyl groups includes, for example, trifluoromethyl, trichloromethyl and chloro-difluoromethyl groups. The alkylene group represented by $-C_nH_{2n}-$ is a straight or branched chain alkylene grpoup having 1 to 4 carbon atoms, and includes, for example, methylene, ethylene, 1-methylethylene, 2-methylethylene, trimethylene, 1-methyltrimethylene and 2-methyltrimethylene groups. The hetero cyclic group represented by

includes, for example, pyrrolidino, piperidino, piperazino and morpholino groups and substituted derivatives thereof.

The quinazolinone derivatives represented by the aforesaid formula [I] and the pharmaceutically acceptable acid-addition salts (e.g. hydrochloric acid-, hydrobromic acid-, sulfuric acid-, phosphoric acid-, acetic acid-, maleic acid-, fuamric acid-, tartaric acid-, succinic acid- or citric acid- addition salt) of such compounds, which include novel compounds, have excellent pharmacological properties, particularly as central neruous system depressant, anti-inflammatory, analgesic, uricosuric and anti-microbial activities, and they are also useful as intermediates for preparing other quinazoline derivatives. The quinazolinone derivatives or salts thereof of the present invention may be administered parentally or orally in therapeutic dosage forms with dosage adjusted to individual needs, that is, in solid or liquid dosage forms such as tablets, dragees, capsules, suspensions, solutions, elixirs and the like.

A few processes for producing some of these quinazolinone derivatives have heretofore been described. For instance, they are prepared by reacting a 2-aminobenzophenone derivative with an alkylisocyanate and further reducing the resulting 3-alkyl-2(3H)-quinazolinone derivatives. (W. Metlesics et al, J. Org. Chem., 31, 1007 (1966))

Contrary to these procedures, we have found that 3,4-dihydro-2(1H)-quinazolinone derivatives of the formula [I] can be smoothly and economically prepared in high yields and in high purity by the process of the present invention.

Thus, an object of the present invention is to provide a novel process for producing commercially such valuable quinazolinone derivatives.

Another object of the present invention is to provide novel 3,4-dihydro-2(1H)-quinazolinone derivatives.

Other objects and merits of the present invention will be apparent from the following description.

According to the present inventon, 3,4-dihydro-2(1H)-quinazolinone derivatives of the aforesaid formula [I], are produced by the following novel process comprising a. reducing a compound represented by the formula,

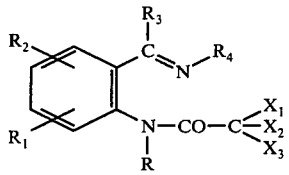
[II]

wherein R, $R_1$, $R_2$, $R_3$ and $R_4$ have the same meanings as defined in the formula [I]; and $X_1$, $X_2$ and $X_3$ signify individually a halogen atom, or further, b. reacting a compound represented by the formula,

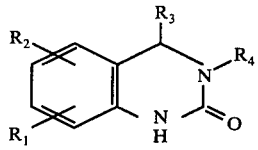
[I-a]

wherein $R_1$, $R_2$, $R_3$ and $R_4$ have the same meanings as defined above, with a reactive ester of an alcohol represented by the formula,

R'-OH [III]

wherein R' signifies any of the substituent represented by the aforesaid R in the formula [I] other than the hydrogen atom.

Still further, according to the present invention, novel 3,4-dihydro-2(1H)-quinazolinone derivatives of the formula,

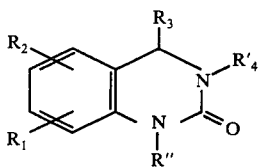
[I-b]

wherein $R_1$, $R_2$ and $R_3$ have the same meanings as defined above, $R'_4$ signifies a lower alkyl group, a lower alkenyl group, an aralkyl group, a lower cycloalkylalkyl group, a lower alkoxyalkyl group, a lower hydroxyalkyl group, a lower alkylthioalkyl group, a lower alkanoyloxyalkyl group, or a group of the formula

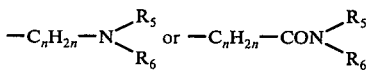

(wherein n, $R_5$ and $R_6$ signify the same as defined above); and R" signifies any of the substituent represented by the aforesaid R in the formula (I) other than the hydrogen atom and the lower alkyl group, may be prepared by a process comprising c. reacting a compound represented by the formula

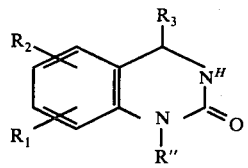
[I-c]

wherein $R_1$, $R_2$, $R_3$ and R" have the same meanings as defined above, with a reactive ester of an alcohol represented by the formula, $R'_4$-OH [III-a]

wherein $R'_4$ has the same meanings as defined above.

Furthermore, the process of the present invention will be explained in detail below.

In the process (a), the quinazolinone derivative of the formula [I] is prepared by reacting the compound of the formula [II] with a suitable reducing agent in the presence of a solvent.

The suitable reducing agents are, for example, complex metal hydrides such as sodium borohydride, lithium borohydride, diisobutylaluminum hydride or mixed metal hydrides or hydrogen together with a metal catalyst such as nickel, palladium, platinum oxide, copper or cobalt. Besides, other conventional methods for reducing a carbon-nitrogen double bond may be employed in this reaction.

Tbe suitable solvents are, for example, methanol, ethanol, isopropanol, methylene chloride, chloroform, carbon tetrachloride, ether, tetrahydrofuran, dimethylformamide, diethylforamide, dimethylacetamide, water, acetic acid and formic acid. The reaction may easily proceed at room temperature, but, if necessary, higher or lower temperatures may be employed to effect the reaction under a desired control.

The starting material of the formula [II] used in the present invention is easily prepared, for example, by reacting a trihalogenoacetanilide derivative represented by the formula,

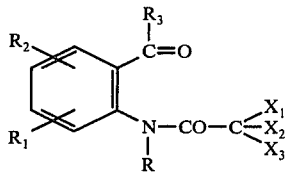
[IV]

wherein R, $R_1$, $R_2$, $R_3$, $X_1$, $X_2$ and $X_3$ have the same meanings as defined above, with an amine, represented by the formula, $R_4$-$NH_2$ [V]

wherein $R_4$ has the same meanings as defined previously, or salt thereof in the presence of a solvent such as an alcohol or the like.

In the process (b), the quinazolinone derivative of the formula [I] is prepared by reacting the compound of the aforesaid formula [I-a] with the reactive ester of the compound of the formula [III] in the presence of a basic condensing agent or alternatively by treating the said compound with a basic condensing agent in a solvent to form a basic metal salt and then reacting the metal salt with the reactive ester of the compound of the formula [III].

As the reactive ester of the compound of the formula [III], there may be preferably used a hydrohalic acid ester such as chloride, bromide or iodide; a sulfonic acid ester such as methanesulfonic acid ester, trichloromethanesulfonic acid ester or p-toluenesulfonic acid ester and a sulfuric acid ester.

The suitable basic condensing agents include, for example, sodium hydride, potassium hydride, sodium amide, potassium amide, butyllithium, phenyllithium, sodium methylate, potassium methylate, sodium ethylate and potassium ethylate.

The suitable solvents, include, for example, benzene, toluene, xylene, monochlorobenzene, dimethylacetamide, diethylacetamide, dimethylformamide, ether, tetrahydrofuran, dioxane and dimethyl sulfoxide.

The reaction is generally effected at a temperature within the range between room temperature and the boiling point of the solvent used.

In the process (c), the quinazolinone derivative of the formula [I-b] is prepared by reacting the compound of the formula [I-c] with the reactive ester of the compound of the formula [III-a] in the presence of a basic condensing agent or alternatively by treating the said compound with a basic condensing agent in a solvent to form a basic metal salt and then reacting the metal salt with the reactive ester of the compound of the formula [III-a]. The reaction may be carried out in the same conditions as described in the process (b).

According to the process of the present invention, there are prepared, for example, the following 3,4-dihydro-2(1H)-quinazolinone derivatives:

3-Methyl-4-phenyl-6-chloro-3,4-dihydro-2(1H)-quinazolinone

3-Ethyl-4-phenyl-6-chloro-3,4-dihydro-2(1H)-quinazolinone

3-Isopropyl-4-phenyl-6-chloro-3,4-dihydro-2(1H)-quinazolinone

3-Allyl-4-phenyl-6-chloro-3,4-dihydro-2(1H)-quinazolinone

3-Cyclopropylmethyl-4-phenyl-6-chloro-3,4-dihydro-2(1H)-quinazolinone 3-($\beta$-Ethoxyethyl)-4-phenyl-6-chloro-3,4-dihydro-2(1H)-quinazolinone 3-($\beta$-Acetoxyethyl)-4-phenyl-6-chloro-3,4-dihydro-2(1H)-quinazolinone 3-($\beta$-Methylthioethyl)-4-phenyl-6-chloro-3,4-dihydro-2(1H)-quinazolinone 3-($\beta$-Diethylaminoethyl)-4-phenyl-6-chloro-3,4-dihydro-2(1H)-quinazolinone 3-($\beta$-Piperidinoethyl)-4-phenyl-6-chloro-3,4-dihydro-2(1H)-quinazolinone 3-($\beta$-Morpholinoethyl)-4-phenyl-6-chloro-3,4-dihydro-2(1H)-quinazolinone 3-(N,N-Dimethylcarbamoylmethyl)-4-phenyl-6-chloro-3,4-dihydro-2(1H)-quinazolinone 3-(p-Chlorophenyl)-4-phenyl-6-chloro-3,4-dihydro-2(1H)-quinazolinone 3-(m-Methoxyphenyl)-4-phenyl-6-chloro-3,4-dihydro-2(1H)-quinazolinone 3-(o-Tolyl)-4-phenyl-6-chloro-3,4-dihydro-2(1H)-quinazolinone 3-(m-Trifluoromethylphenyl)-4-phenyl-6-chloro-3,4-dihydro-2(1H)-quinazolinone 3-(2'-Pyridyl)-4-phenyl-6-chloro-3,4-dihydro-2(1H)-quinazolinone 3-Ethyl-4-phenyl-6-methyl-3,4-dihydro-2(1H)-quinazolinone 3-Ethyl-4-phenyl-6-methoxy-3,4-dihydro-2(1H)-quinazolinone 3-($\beta$-Diethylaminoethyl)-4-phenyl-8-chloro-3,4-dihydro-2(1H)-quinazolinone 3-($\beta$-Piperidinoethyl)-4-phenyl-6-nitro-3,4-dihydro-2(1H)-quinzaolinone 3-($\gamma$-Pyrrolidinopropyl)-4-phenyl-6-chloro-3,4-dihydro-2(1H)-quinazolinone 3-Benzyl-4-phenyl-6-chloro-3,4-dihydro-2(1H)-quinazolinone 3-($\beta$-Hydroxyethyl)-4-phenyl-6-chloro-3,4-dihydro-2(1H)-quinzolinone 3-Cyclohexyl-4-phenyl-6-chloro-3,4-dihydro-2(1H)-quinazolinone 3-($\beta$-Diethylaminoethyl)-4phenyl-6-nitro-3,4-dihydro-2(1H)-quinazolinone 3-($\gamma$-Dimethylaminopropyl)-4-phenyl-6-trifluoromethyl-3,4-dihydro-2(1H)-quinazolinone 3-($\beta$-Piperidinoethyl)-4-phenyl-6-methylthio-3,4-dihydro-2(1H)-quinazolinone 3-Ethyl-4-(2'-furyl)-6-chloro-3,4-dihydro-2(1H)-quinazolinone 3-Ethyl-4-(2'-thienyl)-3,4-dihydro-2(1H)-quinazolinone 3-Ethyl-4-(2'-pyridyl)-6-chloro-3,4-dihydro-2(1H)-quinazolinone 3-($\beta$-Diethylaminoethyl)-4-cyclohexyl-6-chloro-3,4-dihydro-2(1H)-quinazolinone 1,3-Dimethyl-4-phenyl-6-chloro-3,4-dihydro-2(1H)-quinazolinone 1-Methyl-3-($\beta$-ethoxyethyl)-4-phenyl-6-chloro-3,4-dihydro-2(1H)-quinazolinone 1-Methyl-3-($\beta$-morpholinoethyl)-4-phenyl-6-chloro-3,4-dihydro-2(1H)-quinazolinone 1-Methyl-3-($\beta$-diethylaminoethyl)-4-phenyl-6-chloro-3,4-dihydro-2(1H)-quinazolinone 1-Ethyl-3-($\beta$-dimethylaminoethyl)-4-phenyl-6-chloro-3,4-dihydro-2(1H)-quinazolinone 1-($\beta$-Ethoxyethyl)-3-($\beta$-diethylaminoethyl)-4-phenyl-6chloro-3,4-dihydro-2(1H)-quinazolinone 1,3-Di($\beta$-ethoxyethyl)-4-phenyl-6-chloro-3,4-dihydro-2(1H)-quinazolinone 1-Cyclopropylmethyl-3-cyclohexyl-4-phenyl-6-chloro-3,4-dihydro-2(1H)-quinazolinone 1-Cyclopropylmethyl-3-ethyl-4-(p-methoxyphenyl)-3,4-dihydro-2(1H)-quinazolinone 1-Cyclopropylmethyl-3-($\beta$-diethylaminoethyl)-4-phenyl-6-chloro-3,4-dihydro-2(1H)-quinazolinone 1-Cyclopropylmethyl-3-($\beta$-hydroxyethyl)-4-phenyl-6-chloro-3,4-dihydro-2(1H)-quinazolinone 1-($\beta$,$\beta$,$\beta$-trifluoroethyl)-3-($\beta$-morpholinoethyl)-4-phenyl-6-chloro-3,4-dihydro-2(1H)-quinazolinone 1-Benzyl-3-($\beta$-morpholinoethyl)-4-phenyl-6-chloro-3,4-dihydro-2(1H)-quinazolinone The process of the present invention is illustrated in detail below with reference to examples, but the invention is, of course, not limited only to these.

EXAMPLE 1

A mixture comprising 3.77 g. of 2-trichloroacetamido-5-chlorobenzophenone, 4.08 g. of ethylamine hydrochloride, 5.0 g. of triethylamine and 100 ml. of ethanol was refluxed for 3 hours, and then the solvent was removed under reduced pressure. Thereafter, water was added to the residue, and insoluble crystals were collected by filtration, washed with water and then dried to obtain 3.9 g. of 2-trichloroacetamido-5-chloro-$\alpha$-phenylbenzylideneaminoethane as pale yellow crystals. A part of this compound was recrystallized from ethanol to form colorless prisms having a melting point of 240° – 241° C (decomp.).

Subsequently, 1.21 g. of the 2-trichloroacetamido-5-chloro-α-phenylbenzylideneaminoethane was dissolved in 10 ml. of dimethylformamide. To this solution was portionwise added 0.23 g. of sodium borohydride, and the resulting mixture was stirred at room temperature for 3 hours. Thereafter, the reaction mixture was poured into 50 ml. of water and allowed to stand for a while, and deposited crystals were collected by filtration, washed with water and then dried to obtain 0.8 g. of 3-ethyl-4-phenyl-6-chloro-3,4-dihydro-2(1H)-quinazolinone. This compound was recrystallized from ethanol-chloroform to give colorless prisms having a melting point of 209° – 211° C.

EXAMPLE 2

To a solution of 0.42 g. of 2-(2-trichloroacetamido-5-chloro-α-phenylbenzylideneamino)-ethanol in 5 ml. of dimethylformamide was added 0.08 g. of sodium borohydride, and the resulting mixture was stirred at room temperature for 3 hours. Thereafter, the reaction mixture was poured into 30 ml. of water, extracted with chloroform, washed with water and dried over anhydrous sodium sulfate, and then the solvent was removed under reduced pressure to obtain 0.30 g. of 3-($\beta$-hydroxyethyl)-4-phenyl-6-chloro-3,4-dihydro-2(1H)-quinazolinone. This compound was recrystallized from ethanol-petroleum benzine to give colorless crystals having a melting point of 199° – 200° C.

EXAMPLE 3

Using the procedure similar to that described in Example 2, there were obtained the following 3,4-dihydro-2(1H)-quinazolinone derivatives:

3-Methyl-4-phenyl-6-chloro-3,4-dihydro-2(1H)-quinazolinone, m.p. 224° – 226° C.

3-($\beta$-Acetoxyethyl)-4-phenyl-6-chloro-3,4-dihydro-2(1H)-quinazolinone, m.p. 179° – 180° C.

3-Benzyl-4-phenyl-6-chloro-3,4-dihydro-2(1H)-quinazolinone, m.p. 151° – 152.0° C.

3-(p-Tolyl)-4-phenyl-6-chloro-3,4-dihydro-2(1H)-quinazolinone, m.p. 233° C (decomp.).

3-($\beta$-Diethylaminoethyl)-4-phenyl-6-chloro-3,4-dihydro-2(1H)-quinazolinone, m.p. 182.5° – 183.5° C.

3-($\gamma$-Dimethylaminopropyl)-4-phenyl-6chloro-3,4-dihydro-2(1H)-quinazolinone, m.p. 175° – 177° C (decomp.).

3-($\beta$-Morpholinoethyl)-4-phenyl-6-chloro-3,4-dihydro-2(1H)-quinazolinone, m.p. 186.5° – 187.5° C.

1-Methyl-3-cyclopropylmethyl-4phenyl-6-chloro-3,4-dihydro-2(1H)-quinazolinone, m.p. 106° – 107° C.

1-Cyclopropylmethyl-3-ethyl-4-phenyl-6-chloro-3,4-dihydro-2(1H)-quinazolinone, m.p. 88° – 90° C.

1-Ethyl-3-($\beta$-diethylaminoethyl)-4-phenyl-6-chloro-3,4-dihydro-2(1H)-quinazolinone, m.p. 198° – 199° C (decomp.).

1-Isopropyl-3-($\gamma$-dimethylaminopropyl)-4-phenyl-3,4-dihydro-2(1H)-quinazolinone, oil.

1-Cyclopropylmethyl-3-($\beta$-diethylaminoethyl)-4-phenyl-6-chloro-3,4-dihydro-2(1H)-quinazolinone, oil.

EXAMPLE 4

To a solution of 1.07 g. of 3-($\beta$-diethylaminoethyl)-4-phenyl-6-chloro-3,4-dihydro-2(1H)-quinazolinone in 20 ml. of dimethylformamide was added 0.13 g. of 64% sodium hydride, and the resulting mixture was heated with stirring at 60° C (bath temperature) for 1 hour. Thereafter, 0.94 g. of ethyl iodide was added thereto at room temperature, and the mixture was stirred at 100° C (bath temperature) for 4 hours. After cooling, the reaction mixture was poured into 100 ml. of water, extracted with chloroform, washed with water and dried over anhydrous sodium sulfate, and then the solvent was removed under reduced pressure to obtain colorless oily 1-ethyl-3-($\beta$-diethylaminoethyl)-4-phenyl-6-chloro-3,4-dihydro-2(1H)-quinazolinone hydroiodide. This compound was crystallized from ethanol-petroleum benzine to give colorless fine crystals having a melting point of 198°–199° C (decomp.).

EXAMPLE 5

Using the procedure similar to that described in Example 4, there were obtained the following 3,4-dihydro-2(1H)-quinazolinone derivatives:

1-Methyl-3-($\beta$-dimethylaminoethyl)-4-phenyl-3,4-dihydro-2(1H)-quinazolinone (maleate), m.p. 142° C.

1-Cyclopropylmethyl-3-($\beta$-diethylaminoethyl)-4-phenyl-6-chloro-3,4-dihydro-2(1H)-quinazolinone, oil.

1-Methyl-3-cyclopropylmethyl-4-phenyl-6-chloro-3,4-dihydro-2(1H)-quinazolinone, m.p. 106°–207° C.

1-Cyclopropylmethyl-3-ethyl-4-phenyl-6-chloro-3,4-dihydro-2(1H)-quinazolinone, m.p. 88°–90° C.

EXAMPLE 6

To a solution of 3.1 g. of 1-cyclopropylmethyl-4-phenyl-6-chloro-3,4-dihydro-2(1H)-quinazolinone in 50 ml. of dimethylformamide was added 0.42 g. of 63% sodium hydride, and the resulting mixture was stirred at 50° C. for 30 minutes. Thereafter, 3.1 g. of ethyl iodide was added, and the mixture was stirred at 60° C. for 4 hours. After cooling, the reaction mixture was poured into 300 ml. of water and extracted with chloroform, and the chloroform layer was washed with water, dried over anhydrous sodium sulfate and then concentrated under reduced pressure. The residue was adsorbed on a silica gel column, eluted with chloroform to obtain yellow oily 1-cyclopropylmethyl-3ethyl-4-phenyl-6-chloro-3,4-dihydro-2(1H)-quinazolinone. Crystallization from petroleum benzine gave colorless prisms having a melting point of 88°–90° C.

EXAMPLE 7

To a solution of 3.1 g. of 1-cyclopropylmethyl-4-phenyl-6-chloro-3,4-dihydro-2(1H)-quinazolinone in 50 ml. of dimethylformamide was added 0.42 g. of 63% sodium hydride, and the resulting mixture was stirred at 50° C. for 30 minutes. Thereafter, 2.7 g. of $\beta$-diethylaminoethyl chloride was added, and the mixture was stirred at 100° C. for 8 hours. After cooling, the reaction mixture was poured into 300 ml. of water, and ammonia water was added thereto to make alkaline. The resulting mixture was extracted with benzene. The benzene layer was washed with water and dried, and then the solvent was removed under reduced pressure. The residue was dissolved in 50 ml. of ether, and the insoluble material were separated by filtration. The filtrate was extracted with 50 ml. of 5% hydrochloric acid, and the water layer was further washed with ether, made alkaline by addition of ammonia water and then extracted with ether. The ether layer was washed with water and dried over anhydrous sodium sulfate, and then the solvent was removed to obtain oily 1-cyclopropylmethyl-3-($\beta$-diethylaminoethyl)-3,4-dihydro-4-phenyl-6-chloro-2(1H)-quinazolinone.

What is claimed is:

1. A 3,4-dihydro-2(1H)-quinazolinone derivative represented by the formula, wherein $R_1$ and $R_2$ signify individually a hydrogen atom, a lower alkyl group, a lower alkoxy group, a nitro group, a trifluoromethyl group, a lower alkylthio group, a lower alkylsulfonyl group or a halogen atom; $R_3$ is phenyl, halophenyl, lower alkylphenyl, lower alkoxyphenyl, trifluoromethylphenyl or naphthyl; and $R''_4$ is a group of the formula $$-C_nH_{2n}-N{<}^{R_5}_{R_6} \text{ or } -C_nH_{2n}-CON{<}^{R_5}_{R_6}$$

wherein n signifies an integer of 1 to 4, and $R_5$ and $R_6$ signify individually lower alkyl.

2. A quinazolinone derivative of the formula,

[V]

wherein $R_1$ and $R_2$ are independently hydrogen, lower alkyl, lower alkoxy, nitro, trifluoromethyl, lower alkylthio, lower alkylsulfonyl or halogen; $R_3$ is phenyl, halophenyl, lower alkylphenyl, lower alkoxyphenyl, trifluoromethylphenyl or naphthyl; and $R''_4$ is a group of the formula $$-C_nH_{2n}-N{<}^{R_5}_{R_6} \text{ or } -C_nH_{2n}-CON{<}^{R_5}_{R_6}$$

wherein n signifies an integer of 1 to 4 and $$-N{<}^{R_5}_{R_6}$$

forms piperidino or morpholino.

3. A quinazolinone derivative according to claim 1 which is 3-(β-diethylaminoethyl)-4-phenyl-6-chloro-3,4-dihydro-2(1H)-quinazolinone.

4. 3,4-Dihydro-2(1H)-quinazolinone derivatives represented by the formula,

[I-d]

wherein $R_1$ and $R_2$ are individually a hydrogen atom or a halogen atom; $R_3$ is a phenyl group; and $R''_4$ is a group of the formula $$-C_nH_{2n}-N{<}^{R_5}_{R_6}$$

wherein n signifies an integer of 1 to 4 and $$-N{<}^{R_6}_{R_5}$$

forms piperidino or morpholino.

5. A compound according to claim 4 wherein $R_1$ is hydrogen and $R_2$ is 6-halogeno.

6. A compound according to claim 4 wherein $R_1$ is hydrogen and $R_2$ is 6-chloro.

7. 3-(β-Morpholinoethyl)-4-phenyl-6-chloro-3,4-dihydro-2(1H)-quinazolinone.

8. A process for preparing 3,4-dihydro-2(1H)-quinazolinone drivatives represented by the formula,

[I]

wherein $R_1$ and $R_2$ signify individually a hydrogen atom, a lower alkyl group, a lower alkoxy group, a nitro group, a trifluoromethyl group, a lower alkylthio group, a lower alkylsulfonyl group or a halogen atom; $R_3$ signifies a phenyl group, a halophenyl group, a lower alkylphenyl group, a lower alkoxyphenyl group, a trifluoromethylphenyl group, a lower cycloalkyl group, a lower cycloalkenyl group, a pyridyl group, a pyrrolyl group, a furyl group, a thienyl group or a naphthyl group; $R_4$ signifies a lower alkyl group, a lower alkenyl group, an aralkyl group, a lower cycloalkylalkyl group, a lower cycloalkyl group, a lower alkoxyalkyl group, a lower alkylthioalkyl group, a lower hydroxyalkyl group, a lower alkanoyloxyalkyl group, a phenyl group, a halophenyl group, a trifluoromethylphenyl group, a lower alkylphenyl group, a lower alkoxyphenyl group, a pyridyl group or a group of the formula $$-C_nH_{2n}-N{<}^{R_5}_{R_6} \text{ or } -C_nH_{2n}-CON{<}^{R_5}_{R_6}$$

(wherein n signifies an integer of 1 to 4; and $R_5$ and $R_6$ signify individually a lower alkyl group, provided that they may form together with the adjacent nitrogen atom an optionally substituted 5- or 6-membered heterocyclic ring, which may further contain a hetero atom); and R signifies a hydrogen atom, a lower alkyl group, a lower alkenyl group, a lower alkoxyalkyl group, a lower alkylthioalkyl group, an aralkyl group, a lower cycloalkylalkyl group, a lower trihalomethylalkyl group or a group of the formula

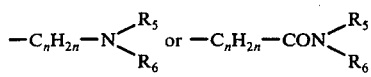

(wherein $n$, $R_5$ and $R_6$ signify the same as defined above), which comprises reducing in a solvent with a reducing agent selected from the group consisting of (a) complex metal hydrides and (b) hydrogen together with a catalyst, a compound represented by the formula,

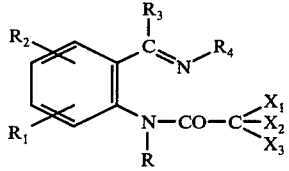

wherein R, $R_1$, $R_2$, $R_3$ and $R_4$ have the same meanings as defined above; and $X_1$, $X_2$ and $X_3$ signify individually a halogen atom.

9. Process according to claim 8, wherein $R_1$ and $R_2$ are as defined in claim 8; $R_3$ is phenyl, halophenyl, lower alkylphenyl, lower alkoxyphenyl, trifluoromethylphenyl or naphthyl; $R_4$ is a group of the formula

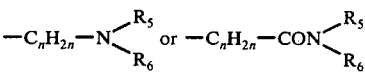

wherein $n$ signifies an integer of 1 to 4, and $R_5$ and $R_6$ signify individually lower alkyl group; and R is hydrogen, lower alkyl, lower alkenyl, lower alkoxyalkyl, lower alkylthioalkyl, aralkyl, lower cycloalkylalkyl, or lower trihalomethylalkyl.

10. A process according to claim 8, wherein the solvent is at least one member selected from the group consisting of methanol, ethanol, isopropanol, methylene chloride, chloroform, carbon terachloride, ether, tetrahydrofuran, dimethylformamide, diethylformamide, dimethylacetamide, water, acetic acid and formic acid.

11. A process according to claim 8, wherein in the starting material of the formula [II] R is a hydrogen atom, a lower alkyl group, a lower alkenyl group, a lower cycloalkylalkyl group or a lower alkoxyalkyl group.

* * * * *